United States Patent
Häubl

(10) Patent No.: US 10,456,340 B2
(45) Date of Patent: Oct. 29, 2019

(54) LIQUID-IMPREGNATED NONWOVEN FABRIC WHICH CONTAINS ZINC OXIDE-CONTAINING CELLULOSE FIBERS

(71) Applicant: LENZING AG, Lenzing (AT)

(72) Inventor: Martin Häubl, Linz (AT)

(73) Assignee: Lenzing Aktiengesellschaft, Lenzing (AT)

( * ) Notice: Subject to any disclaimer, the term of this patent is extended or adjusted under 35 U.S.C. 154(b) by 0 days.

(21) Appl. No.: 15/518,686

(22) PCT Filed: May 12, 2015

(86) PCT No.: PCT/AT2015/000073
§ 371 (c)(1),
(2) Date: Apr. 12, 2017

(87) PCT Pub. No.: WO2016/065376
PCT Pub. Date: May 6, 2016

(65) Prior Publication Data
US 2017/0239153 A1   Aug. 24, 2017

(30) Foreign Application Priority Data
Oct. 28, 2014   (AT) .................................... 790-2014

(51) Int. Cl.
| | | |
|---|---|---|
| *A61K 8/27* | (2006.01) | |
| *A61K 8/81* | (2006.01) | |
| *A61K 8/02* | (2006.01) | |
| *D01F 1/02* | (2006.01) | |
| *D04H 1/425* | (2012.01) | |
| *D01F 1/10* | (2006.01) | |
| *D01F 2/00* | (2006.01) | |
| *A61Q 1/14* | (2006.01) | |
| *A61K 8/73* | (2006.01) | |
| *A61Q 17/00* | (2006.01) | |
| *A61Q 19/10* | (2006.01) | |
| *A61Q 19/00* | (2006.01) | |

(52) U.S. Cl.
CPC .............. *A61K 8/27* (2013.01); *A61K 8/0208* (2013.01); *A61K 8/731* (2013.01); *A61K 8/8147* (2013.01); *A61Q 1/14* (2013.01); *A61Q 17/005* (2013.01); *A61Q 19/00* (2013.01); *A61Q 19/10* (2013.01); *D01F 1/103* (2013.01); *D01F 2/00* (2013.01); *A61K 2800/524* (2013.01); *A61K 2800/624* (2013.01); *A61K 2800/651* (2013.01); *A61K 2800/74* (2013.01)

(58) Field of Classification Search
None
See application file for complete search history.

(56) References Cited

U.S. PATENT DOCUMENTS

| | | | | |
|---|---|---|---|---|
| 2,114,915 | A * | 4/1938 | Davis | ........................ D01F 2/06 264/179 |
| 6,416,859 | B1 | 7/2002 | Caswell et al. | |
| 8,435,625 | B2 | 5/2013 | Ruehe et al. | |
| 9,243,349 | B2 | 1/2016 | Kolbe et al. | |
| 2004/0055704 | A1* | 3/2004 | Bunyard | ................. A61L 15/24 156/305 |
| 2006/0171971 | A1 | 8/2006 | Marsh et al. | |
| 2008/0318004 | A1 | 12/2008 | Ruhe et al. | |
| 2009/0004474 | A1 | 1/2009 | Luo | |
| 2010/0143652 | A1* | 6/2010 | Stockton | .............. A61K 8/0208 428/141 |
| 2011/0135701 | A1 | 6/2011 | Kolbe et al. | |
| 2011/0152433 | A1* | 6/2011 | Bechtloff | ................. A61K 8/19 524/460 |
| 2011/0224637 | A1 | 9/2011 | Edgett et al. | |
| 2011/0293931 | A1* | 12/2011 | Vogel | ................... A61K 8/0208 428/340 |
| 2012/0177919 | A1 | 7/2012 | Kroner | |
| 2012/0215148 | A1 | 8/2012 | Ewert et al. | |

FOREIGN PATENT DOCUMENTS

| | | |
|---|---|---|
| CN | 101985781 A | 3/2011 |
| DE | 202010010803 U1 | 12/2010 |
| DE | 202011000227 U | 3/2011 |
| DE | 202011002709 U | 4/2011 |
| DE | 202012011814 U1 | 1/2013 |
| EP | 1 093 536 B1 | 1/2003 |
| EP | 1 618 240 B1 | 1/2006 |
| EP | 2 334 853 B1 | 6/2011 |
| JP | 2006-249615 A | 9/2006 |
| JP | 2007-191801 A | 8/2007 |
| WO | 99/59540 A1 | 11/1999 |
| WO | 2004/081267 A1 | 9/2004 |
| WO | 2005083162 A1 | 9/2005 |
| WO | 2007/022552 A1 | 3/2007 |

(Continued)

OTHER PUBLICATIONS

Wiegand et al., Clinical, Cosmetic and Investigational Dermatology, 6, pp. 115-121. (Year: 2013).*

(Continued)

*Primary Examiner* — Abigail Vanhorn

(74) *Attorney, Agent, or Firm* — Venable LLP

(57) ABSTRACT

The present invention relates to a formed fabric which contains cellulose fibers, which contain zinc oxide particles which are at least partially incorporated and which is additionally impregnated with a liquid, and to a method of its production and to its use, in particular for manufacturing preservative-free, moist wet wipes.

14 Claims, No Drawings

(56) References Cited

FOREIGN PATENT DOCUMENTS

| WO | 2009/006206 A1 | 1/2009 |
| WO | 2011/026159 A1 | 3/2011 |
| WO | 2012/034679 A1 | 3/2012 |

OTHER PUBLICATIONS

Anitha et al., Carbohydrate Polymers, 97, pp. 856-863. (Year: 2013).*
International Preliminary Report on Patentability and Written Opinion issued in International Application PCT/AT2015/000073 (13 pages).
International Search Report issued in International Application PCT/AT2015/000073 (7 pages).

* cited by examiner

LIQUID-IMPREGNATED NONWOVEN FABRIC WHICH CONTAINS ZINC OXIDE-CONTAINING CELLULOSE FIBERS

The present application is a national-stage entry under 35 U.S.C. § 371 of International Patent Application No. PCT/AT2015/000073, filed May 12, 2015, which claims priority to Austrian Patent Application No. A 790-2014 filed Oct. 28, 2014, the entire disclosure of each of which is incorporated by reference herein.

BACKGROUND OF THE INVENTION

Field of the Invention

The present invention relates to a formed fabric which contains cellulose fibers, which contain zinc oxide particles which are at least partially incorporated and which is additionally impregnated with a liquid, and to a method of its production and to its use, in particular for manufacturing preservative-free wet wipes.

DESCRIPTION OF RELATED ART

Prior Art

Given the background of rapidly changing living conditions and customs including increasing mobility, increasing well-being, greater hygienic requirements and an increasing lank of time, in recent years the need for wet cleaning cloths, so-called wet wipes, which are used to clean hard and soft surfaces, has greatly increased. This concerns carrier materials, preferably fleeces which are treated with an active impregnating solution or one containing active substances, are packaged and are marketed in a moist state, for example as fleeces for refreshment, in the household, in the toilet, for makeup removal or for baby cloths. The main areas of use are cosmetics (personal care, baby care) and in the cleaning of objects. Depending on the area of use, a high cleaning performance and/or a skin-protecting action are important for the product requirements.

In order to prevent microbial contamination, all cosmetic products must have a sufficient preservation according to the Standard for Cosmetic Agents—Microbiology—Evaluation of the Antimicrobial Protection of a Cosmetic Product (ISO 11930). To this end preservative agents are customarily added, which on the one hand ensures the ability to preserve and store the unopened product and on the other hand to prevent the package from being contaminated by germs after it is opened. In the using phase the process of removing the cloth by the end user represents the main entry source for germs. For the purposes of the present invention the concept "preservative agents" denotes the substances defined as such in the Annex VI of the EU Cosmetics Regulation (76/768/EEC), status 03. September 2014.

Preservation agents are antimicrobially active biocides which suppress or inhibit or kill the growth of microorganisms such as bacteria, funguses and yeasts. However, this can also negatively affect the flora on the skin and can express itself in an increased occurrence of skin irritations and skin redness, allergies and eczemas. Therefore, the addition of preservative agents to cosmetic and medical products should be critically viewed especially in the case of damage to sensitive skin such as baby skin. It is uncertain in this connection whether and in which amount such active substances are absorbed by the skin. The position of data regarding toxicology must in many instances be classified as insufficient. Therefore, a few animal experiments allow the supposition that paraben can influence the hormonal system when used for a rather long time. Phenoxyethanol, a frequently used preservative agent possibly has a liver-damaging action.

Therefore, it is necessary to find compatible and at the same time effective alternatives for preservation agents. Zinc oxide has long been used in medicine on account of its antiseptic and inflammation-inhibiting action as an active substance in products for skin care and wound treatment. Salves, plasters or bandages which contain zinc oxide are available which are suitable for use on surfaces for skin redness, rashes and inflammations (for example, diaper dermatitis) and light burns. Zinc is an essential trace element for the human body which significantly influences the prevention forces and the functioning of numerous body enzymes. Therefore, zinc-containing products have a high biological compatibility.

According to the prior art, in the manufacture of moist cloths both the skin-protecting and the healing action of zinc oxide as well as its antimicrobial properties are used in that different, for example cellulosic carrier materials in the form of fleeces are treated with zinc-oxide-containing emulsions or other impregnating solutions. This is described, among other places, in U.S.20060171971 (A1) and in WO9959540 (A1). The cited patents also refer to the option of adding preservative agents to the liquid formulations. The zinc oxide in the application forms described in these documents obviously has only a caring and healing but no preserving action.

A significant disadvantage of these products is that at times high amounts of auxiliary chemicals such as surfactants or thickening agents must be added to the impregnating liquids in order to avoid an undesired settling of the zinc oxide particles during the manufacturing process and the storage of the products which would occur due to the high specific density of the ZnO particles.

The incorporation of zinc oxide and polyolefin masses for the manufacture of non-wovens according to the melt-spinning or melt-blown method in the usage of such antimicrobial products in the areas of medicine and hygiene, for example as moist wiping cloths, is claimed in JP2006249615 (A). However, such non-wovens have, due to the hydrophobic character of the polyolefins, a low suction power and a lower absorption capacity for aqueous liquids and are therefore only very conditionally suitable as moist cloths in combination with water-containing formulations. In addition, these fleeces, in contrast to non-wovens consisting of cellulosic fibers are not biologically degradable.

Cellulosic fibers and chemical fibers such as polyester or polypropylene are to be preferred in the manufacture of moist wiping cloths also on account of their hydrophilicity, which is based on the property of cellulose to form strong hydrogen bridges with water molecules and the associated high absorption power for aqueous liquids. In addition the cellulose, artificial cellulosic fibers, so-called cellulose regenerative fibers such as viscose fibers or lyocell fibers are used. The latter are superior in many areas to natural cellulose fibers as regards uniformity, purity (e.g. pesticide residues), softness and suction properties. In particular lyocell fibers are distinguished by a dry strength and in particular by a wet strength in comparison to other cellulosic fibers and make possible the manufacture of soft end products with high strengths.

Objects of daily use which comprise zinc-oxide-containing lyocell fibers and in addition have antimicrobial or skin-friendly and healing properties are known, for example, from DE202010010803 (U1) in the form of a sensitive wash or from DE202012011814 (U1) in the form of a finger for the oral or dental care for newborns and infants, wherein the latter is also preferably designed in the form of a textile.

Therefore, on the whole, numerous possibilities are cited in the literature for manufacturing cellulosic wet wipes with wound-healing, skin-caring or antimicrobial action. However, these methods are limited to impregnation methods which are characterized in that the carrier materials in the form of fleeces are charged with liquid formulations containing zinc oxide. Preservation agents are frequently added to these impregnation liquids for ensuring their service life as well as other auxiliary substances such as surfactants in order to prevent a settling of the zinc oxide particles in production and storage. However, the use of chemical additives and in particular of preservative agents is undesirable as regards consumer protection and consumer health.

Fleeces with antimicrobial properties manufactured from zinc-oxide-containing lyocell spinning masses according to the melt-blown method are described in WO2009006206 (A1). WO2012034679 (A1) claims spinning fleeces which are manufactured according to known spinning fleece methods from cellulosic solutions doped with metal oxide using N-methylmorpholine-N-oxide as direct solution agent. Both patents discuss the use of such fleeces in the hygienic area but not as moist wipe cloths in particular. In addition, the cited formed fabrics are not only subject to limitations regarding their method of manufacture. Thus, the hemicellulose content of the fleeces described in WO2009006206 (A1) is 4 to 18%; in WO2012034679 (A1) the additive content in the fiber is set at greater than 40 wt %. Therefore, in both instances the mechanical textile properties of the fibers are greatly reduced. These fibers display, among other things, a low tear resistance.

Zinc pigment-containing lyocell fibers are also disclosed in EP 2334853 B1. It describes a special form of such fibers in which the zinc is present at least partially as zincate. It is known to a person skilled in the art that zincate can be present only in an alkaline environment. These fibers should have, among other things, an antibacterial action which is achieved in particular in that in addition to zinc oxide zinc sulfide is also contained in the pigment. The primary goal of these fibers is to retain these properties even after several washings. Since the lotions contain in moist wiping cloths, for example, baby wet wipes, always have an acidic pH, no zincate will occur in such applications. The pH of the human skin is usually about pH 5.5, wherein the lotions in wet wipes are usually somewhat more acidic in order not to negatively influence the skin.

WO 2004081267 A1 concretely discloses in example V there the production of a ZnO-containing lyocell fiber with a certain UV absorption capacity. Concrete usages of these fibers are not cited in WO 2004081267 A1; however, it can be concluded from the specification that WO 2004081267 A1 has the goal of the manufacture of UV-absorbing fibers.

Problem

The problem over the described prior art consisted in making available a formed fabric which when used in moist products to be further worked did not require any additional preservative agent or only a clearly lesser amount of preservative agents than was previously customary, in particular in order to prevent a contamination with germs during the manufacture, storage and removal of these moist products from the package and to minimize the contact of the consumers with such preservative agents. However, this formed fabric show have, in addition to the above-cited functionality, other optimal properties regarding resistance to moisture, moisture absorption, etc.

DESCRIPTION OF THE INVENTION

The solution of the above-described problem consists in making a formed fabric available which contains cellulose fibers, wherein the cellulose fibers contain incorporated zinc oxide particles at least partially and the formed fabric is additionally impregnated with a liquid. The cellulose fibers containing zinc oxide are according to the invention cellulosic artificial fibers, manufactured, e.g. according to the viscose-, modal- or lyocell method, which are basically known to the person skilled in the art. Even the spinning in of solid substances into such fibers is basically known to the person skilled in the art, for example from WO 2011/026159 for viscose spinning solutions or from WO 2007/022552 for lyocell spinning solutions. In addition to other advantages, the formed fabric according to the invention also has anti-allergenic properties on account of the enzyme-deactivating properties of ZnO as well as the absorption of allergenic substances. Another surprising advantages of the present invention is the fact that these properties are achieved here with considerably lesser ZnO contents than is possible according to the prior art (see also the examples described below and table 2).

A formed fabric is preferred in which the liquid has a pH lesser than 7. A formed fabric is especially preferred in which the liquid has a pH between 3 and 6, preferably between 4.5 and 5.5. This is achieved by impregnating the formed fabric with an acidic liquid with an appropriate pH. A preferred embodiment of the present invention is therefore a formed fabric in which the liquid contains an organic or inorganic acid which forms a soluble zinc salt. For the purposes of this invention the term soluble zinc salt should denote a zinc salt which has a solubility of more than 50 ppm in 18-MOhm water at 25° C. and an atmospheric pressure of 1013 hPa. The term "18-MOhm water" generally denotes a water deionized by ion exchangers or other known methods which has a conductivity of a maximum of 18 MOhm.

This acid should be already widely used in cosmetics. This acid is preferably selected from the group containing formic acid, acetic acid, lactic acid, citric acid, gluconic acid, glutamic acid, succinic acid, hydrochloric acid, and sulfuric acid and the soluble zinc salt is accordingly preferably selected from the group containing zinc formiate, zinc acetate, zinc lactate, zinc citrate, zinc gluconate, zinc glutamate, zinc succinate, zinc chloride and zinc sulfate.

The zinc-oxide-incorporated cellulose fibers in the formed fabric of the invention contain between 0.1 and 10 wt % zinc oxide, preferably between 0.3 and 4.5 wt % zinc oxide, in particular preferably between 0.3 and 3.5 wt % zinc oxide relative to absolutely dry cellulose. Even up to 17 wt % zinc oxide is possible but is not frequently used due to economic considerations.

The formed fabric according to the invention can also contain zinc-oxide-free cellulose fibers aside from the zinc-oxide-incorporated cellulose fibers. For this, even natural cellulose fibers such as cotton, hemp, etc. can be considered in addition to the artificial cellulosic fibers manufactured, e.g. according to the viscose-, modal- or lyocell method.

The formed fabric according to the invention can also contain synthetic fibers aside from the zinc-oxide-incorporated cellulose fibers. Basically all known synthetic fibers can be considered for this. Polyethylene terephthalate and polypropylene are especially suitable.

In the formed fabric according to the invention the cellulose fibers are either staple fibers or endless filament fibers. The formed fabrics consisting of endless filament fibers can also comprise the formed fabrics manufactured according to the melt-blown method (see, for example, EP 1093536 B1).

The formed fabric according to the invention has a fiber roughness of 8.5 N or greater—measured with the sledge test described in the examples. It was found that a higher fiber roughness leads to a better cleaning action, among other things also by raising the cleaning surface of the moist wet wipe.

The present invention also has as subject matter a method for the manufacturing of a formed fabric by traditional fleece manufacturing methods in which cellulose fibers containing incorporated zinc oxide are used for the fleece formation and the formed fabric is impregnated with a liquid. Fleece formation methods which can be considered include mechanical fleece formation, hydrodynamic fleece formation, aerodynamic fleece formation and melt blowing; fleece strengthening methods which can be considered include above all water jet strengthening, needling, thermal strengthening and chemical strengthening.

The present invention furthermore has as subject matter the use of a formed fabric which contains zinc-oxide-incorporated cellulose fibers and is impregnated with a liquid for the manufacture of wet wipes, in particular as baby moist wipes, makeup removal cloths, cleaning cloths, etc.

A usage in accordance with the invention is especially preferred in which the wet wipes contain no additional preservative agents. The concept "preservative agents" denotes here the substances listed in Annex VI of the EU Cosmetics Regulation (76/768/EEC), status 03. September 2014.

Therefore, the present invention also comprises wet wipes which contain the above-described formed fabric in accordance with the invention and therefore do not require such additional preservative agents.

An improved cleaning power also occurs by the absorption of anionic dirt (e.g. feces, organic acids, etc.) on ZnO on the surface and in the cross section of the fibers.

The present invention furthermore has as subject matter the use of a formed fabric which contains zinc-oxide-incorporated cellulose fibers and is impregnated with a liquid for the manufacture of moist face masks. Such moist fact masks can be impregnated with substances which have a skin-caring action The ZnO itself, incorporated into the fiber and which is known for its skin-caring action, also contributes to the skin-caring action of the entire product.

The invention is described in the following using examples. However, the invention is expressly not limited to these examples but rather also comprises all other embodiments based on the same inventive concept.

EXAMPLES

Manufacture of the Wet Wipes:

At first, lyocell fibers were manufactured according to the lyocell method known in the prior art, into which 0.0, 1.2, 3.0 and 16.7 wt % (relative to absolutely dry fiber) ZnO were spun so that a spinning mass according to the lyocell process was produced which contained 13 wt % cellulose and the above-cited amount of ZnO (relative to cellulose). This was then spun according to the lyocell process (individual fiber titer 2.5 dtex, cut length 38 mm), provided with a finish which has no preservative or biocidal properties and then dried. Needle fleeces (surface weight 60 g/m$^2$, 300 punctures/cm$^2$) were produced from the fibers manufactured in this manner which were subsequently strengthened with a water jet and then dried (on a Fleissner system with the following settings: 35 bar water pressure; 1 jet beam with 2 nozzle rows; demineralized water: pH 7.6; passage speed of the fleece 2 m/min; 100 µm perforation diameter of the water jet nozzles; 118° C. drying temperature. The fleeces manufactured in this manner were impregnated with 290 wt % lotion (relative to the dry weight of the fleece) in order to obtain corresponding baby wet wipes. The exact composition of the lotion is indicated in table 1. The pH of the lotion was adjusted after 48 h of contact with the formed fabrics to pH 3.00.

TABLE 1

| INCI name | Trade name | Manufacturer | Function | wt % |
|---|---|---|---|---|
| Aqua | Demineralized water | Itself | Solvent | 96.15 g |
| Propylene glycol | Propylene glycol | Sigma Aldrich | Moisture retention agent | 3.00 g |
| Polysorbate 20 | Tween 20 | Sigma Aldrich | Solutizer | 0.60 |
| Capryl/capramidopropyl betaines 35% | Tego betain 810 | Evonik | Surfactant | 0.25 |
| Acetic acid | Acetic acid pA | Sigma Aldrich | pH adjustment | 1.44 |

Test for Sufficient Preservation According to ISO 11930:

Every 100 wet wipes, consisting of fibers with 0.0, 1.2 or 16.7 wt % ZnO with the size 15×10 cm, were impregnated with lotion (290 wt % lotion on dry weight of fleece, composition according to table 1) and then the tests for sufficient preservation were carried out. To this end the wet wipes were injected with an inoculum which contained germs customary in cosmetics in a defined concentration (*S. aureus:* 7.40E+05 KBE; *P. aeruginosa:* 2.80E+05 KBE; *E. coli:* 4.40E+05 KBE; *C. albican:* 6.90E+05 KBE; *A. brasiliensis:* 1.70E+05 KBE). After the injection the wet wipes were stored 28 days. After an observation time of 7, 14 and 28 days the germ count of the microorganisms on the wet wipes was determined (see table 2) in order to be able to determine a reduction of germs.

The tests according to ISO 11930 showed that the preservation regarding the germs customary in cosmetics was successful for the wet wipes with 1.2 and 16.7 wt % ZnO on absolutely dry fibers since a sufficient germ reduction was achieved. The higher amount of ZnO clearly showed a better action (criterion A according to DIN EN 11930) than the lesser concentration of ZnO (criterion B according to DIN EN 11930).

Sleds Test According to EN 1202 PPS:

The softness of the fibers was determined with the sledge test described in EN 1202 PPS. The essential conditions of this test are:

5 g fiber sample were carded twice, for example, on a Uster MTDA-3 rotor ring device. The fibers were conditioned for at least 24 h according to the EDANA regulation (ERT 60.2-99 and then cut by a template. The material is subsequently placed in the test device and a carriage carrying a weight of 2000 g is mounted and placed on the sample. The test is started and after 10 sec the force is measured that is necessary to draw the carriage over the sample. The softer the fiber surface is, the less force is required to draw the carriage forward. The test was repeated four times on each material. The results are shown in the following table 3.

TABLE 2

| ZnO content of the fibers/ wt % | Observation time period [Days] | Germs | | | | | Result |
|---|---|---|---|---|---|---|---|
| | | S. aureus KBE/g | P. aeruginosa KBE/g | E. coli KBE/g | C. albicans KBE/g | A. brasiliensis KBE/g | |
| 0.0 | 7 | 20 | <10 | <10 | $9.4 \times 10E3$ | — | Neither criterion A nor B met on account of insufficient germ reduction. Product displays optically dark spots. |
| | 14 | <10 | <10 | <10 | $3.0 \times 10E5$ | <10 | |
| | 28 | <10 | <10 | <10 | <10 | <10 | |
| 1.2 | 7 | <10 | <10 | <10 | $3.0 \times 10E5$ | — | Meets criterion B according to DIN EN 11930 |
| | 14 | <10 | <10 | <10 | $3.1 \times 10E4$ | <10 | |
| | 28 | <10 | <10 | <10 | 40 | <10 | |
| 16.7 | 7 | <10 | <10 | <10 | $1.5 \times 10E5$ | — | Meets criterion A according to DIN EN 11930 |
| | 14 | <10 | <10 | <10 | $1.5 \times 10E5$ | $3.3 \times 10E4$ | |
| | 28 | <10 | <10 | <10 | $2.0 \times 10E4$ | $4.8 \times 10E4$ | |

TABLE 3

| Sample name | Fiber-fiber friction (average value) [N] | Standard deviation [N] |
|---|---|---|
| 3.0 wt % ZnO | 9.23 | 0.25 |
| 1.2 wt % ZnO | 6.86 | 0.14 |

The invention claimed is:

1. A formed fabric comprising cellulose fibers, wherein the cellulose fibers comprise zinc oxide particles spun into the cellulose fibers and wherein the formed fabric is impregnated with a liquid, wherein the liquid has a pH between 3 and 6.

2. The formed fabric according to claim 1, wherein the liquid comprises an organic or inorganic acid which forms zinc salts which have a solubility of more than 50 ppm in 18-MOhm water at 25° C. and an atmospheric pressure of 1013 hPa.

3. The formed fabric according to claim 1, wherein the cellulose fibers with spun-in zinc-oxide comprise between 0.1 and 10 wt % zinc oxide relative to absolutely dry cellulose.

4. The formed fabric according to claim 3, wherein the cellulose fibers with spun-in zinc-oxide comprise between 0.3 and 4.5 wt % zinc oxide relative to absolutely dry cellulose.

5. The formed fabric according to claim 4, wherein the cellulose fibers with spun-in zinc-oxide comprise between 0.3 and 3.5 wt % zinc oxide relative to absolutely dry cellulose.

6. The formed fabric according to claim 1, further comprising zinc-oxide-free cellulose fibers.

7. The formed fabric according to claim 1, further comprising synthetic fibers.

8. The formed fabric according to claim 1, wherein the cellulose fibers are selected from the group consisting of staple fibers and endless filament fibers.

9. The formed fabric according to claim 1, wherein said fiber has a fiber-fiber friction of 8.5 N or higher measured with the sledge test.

10. The formed fabric according to claim 3, wherein the liquid has a pH between 4.0 and 5.5.

11. A method for the manufacturing of a formed fabric by traditional fleece manufacturing methods, comprising providing cellulose fibers which comprise spun-in zinc oxide, wherein the cellulose of fibers form fleece and that the formed fabric is impregnated with a liquid, wherein the liquid has a pH between 3 and 6.

12. A moist wet wipe comprising a formed fabric which comprises cellulose fibers with spun-in zinc-oxide, wherein said wipe is impregnated with a liquid, wherein the liquid has a pH between 3 and 6.

13. The wipe according to claim 12, wherein the wipe comprises no additional preservative agents.

14. A moist face mask comprising a formed fabric which comprises cellulose fibers with spun-in zinc-oxide, wherein said mask is impregnated with a liquid having a pH between 3 and 6 and wherein said mask has skin-caring action.

* * * * *